United States Patent
Chambers et al.

(10) Patent No.: US 6,300,511 B1
(45) Date of Patent: Oct. 9, 2001

(54) CATALYZED FLUORINATION OF CARBONYL COMPOUNDS

(75) Inventors: Richard Dickinson Chambers; John Hutchinson, both of Durham; John Stewart Moilliet, Salwick, all of (GB)

(73) Assignee: F2 Chemicals Limited, Preston (GB)

( * ) Notice: Subject to any disclaimer, the term of this patent is extended or adjusted under 35 U.S.C. 154(b) by 0 days.

(21) Appl. No.: 09/463,030

(22) PCT Filed: Jul. 16, 1998

(86) PCT No.: PCT/GB98/01905

§ 371 Date: Mar. 27, 2000

§ 102(e) Date: Mar. 27, 2000

(87) PCT Pub. No.: WO99/03802

PCT Pub. Date: Jan. 28, 1999

(30) Foreign Application Priority Data

Jul. 18, 1997 (GB) .................................... 9715139
Jul. 18, 1997 (GB) .................................... 9715140
Apr. 25, 1998 (GB) .................................... 9808777

(51) Int. Cl.$^7$ ............................ C07F 9/02; C07C 255/07; C07C 69/72; C07C 315/04
(52) U.S. Cl. .................... 558/194; 558/435; 560/178; 560/180; 560/184; 564/197; 568/35
(58) Field of Search ..................... 558/194, 435; 560/178, 180, 184; 564/197; 568/35

(56) References Cited

U.S. PATENT DOCUMENTS 5,569,778 * 10/1996 Umemoto et al. ................... 560/121

FOREIGN PATENT DOCUMENTS

| 271272 A2 | 6/1988 | (EP) . |
| 354444 A2 | 8/1988 | (EP) . |
| 667332 A1 | 8/1995 | (EP) . |
| WO95/14646 | 6/1995 | (WO) . |

OTHER PUBLICATIONS

Organic Reactions vol. 11, (1949) pp. 69–71.*
Morrison, R.T. and Boyd, R.N., "Organic Chemistry," 2nd Ed., Allyn and Boyd, 1966, pp. 579–581, 616–617 and 680.

* cited by examiner

Primary Examiner—Floyd D. Higel
Assistant Examiner—Ebenezer Sackey
(74) Attorney, Agent, or Firm—Myers Bigel Sibley & Sajovec, P.A.

(57) ABSTRACT

The present invention provides a method of substituting a carbonyl compound with fluorine at the α-position, comprising reaching the carbonyl compound with a fluorinating present of a metal-containing catalyst. The reaction results in replacement of a hydrogen atom by fluorine. The catalyst, which is used in a catalytically effective amount, is preferably a transition metal. In one class of methods the catalyst is a transition metal compound. In another class of methods, the catalyst is an elemental metal, in which case the carbonyl compound has an activating group attached to the carbon atom which is substituted by fluorine.

27 Claims, 2 Drawing Sheets

CATALYZED FLUORINATION OF CARBONYL COMPOUNDS

Figure 1:
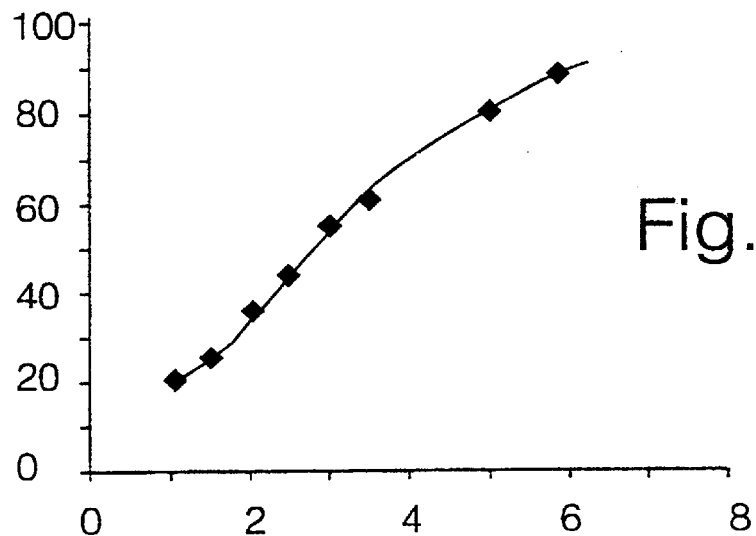

This invention relates to the fluorination of organic compounds, in particular, to the fluorination of carbonyl compounds especially those having a carbonyl, nitro, nitrile sulphonyl or phosphoryl group in the 3-position to the arbonyl group, notably 1,3-dicarbonyl compounds (also known as β-dicarbonyl compounds).

Fluorinated carbonyl compounds, for example fluorinated 1,3-dicarbonyl compounds, are very valuable intermediates in the synthesis of other fluorine-containing compounds. International Patent Application No PCT/GB94102547 describes how treating solutions of 1,3-dicarbonyl compounds in various solvents with elemental fluorine gives the corresponding 2-fluoro-1,3-dicarbonyl compounds. Unfortunately, the fluorination of certain 1,3-dicarbonyl compounds proceeds at an undesirably low rate. Surprisingly, we have now found that the fluorination not only of 1,3-dicarbonyl compounds but also of other carbonyl compounds is catalysed by compounds of transition metals.

The present invention provides a method of substituting a carbonyl compound with fluorine at the α-position, comprising reacting the carbonyl compound with a fluorinating agent in the presence of a metal-containing catalyst. The reaction results in replacement of a hydrogen atom by fluorine. The catalyst, which is used in a catalytically effective amount, is preferably a transition metal. In one class of methods the catalyst is a transition metal compound. In another class of methods, the catalyst is an elemental metal, in which case the carbonyl compound has an activating group attached to the carbon atom which is substituted by fluorine.

The invention also provides a method of fluorinating a 1,3-dicarbonyl compound comprising reacting the 1,3-dicarbonyl compound with a fluorinating agent in the presence of a compound of a transition metal. The reaction results in replacement of a hydrogen atom by fluorine.

A further aspect resides in a process for the fluorination of a β-dicarbonyl compound by means of a fluorinating agent, the process being carried out in the presence of a metal-containing catalyst, the metal preferably being a transition metal.

Methods Catalysed by a Transition Metal Compound

The transition metal compound is preferably a salt. The transition metal is usually a first row transition metal. Exemplary transition metals are those of Groups VIIa, VIII, Ib and IIb. More specific examples of compounds which may be used as catalysts in a method of the present invention are salts and other compounds of copper, iron. cobalt. nickel, manganese or zinc. The identity of the anion of the salt is not critical; suitably it is nitrate, sulphate or acetate of which nitrate is particularly convenient. A mixture of compounds of two or more metals may be used.

Any amount of catalyst may be added to the fluorination reaction but the amount is suitably up to 25 gram atoms of transition metal ion, and preferably 0.2 to 2.5 gram atoms, to 100 moles of substrate. More preferably, the amount of catalyst added is in the range 0.5 to 10 gram atoms of transition metal ion to 100 moles of substrate.

A preferred fluorinating agent is elemental fluorine.

The carbonyl group serves to activate the α-hydrogen which is replaced. The method works well with, inter alia, compounds in which the carbonyl group is ketonic but this feature is far from critical (for example, esteric carbonyl groups are also very suitable). The compounds which are fluorinated preferably have another activating group attached to the carbon atom which is substituted by fluorine, for example another CO group or $(R'O)_2PO$, $SO_2$ or CN; $R'$ is in principle any organic group compatible with the reaction, e.g. alkyl, cycloalkyl or aryl. 1,3-Dicarbonyl compounds are a very preferred class of carbonyl compounds.

More particularly, the starting compounds are preferably of the formula (A): $RCO.CHR^1.R^2$, where:

R is selected from the group consisting of alkyl, oxyalkyl (i.e. —O-alkyl), cycloalkyl, oxycycloalkyl, aryl and oxyaryl;

$R^1$ is selected from the group consisting of $CO.R^3$, $CO.OR^3$, $NO_2$, CN, $CO.NR^3_2$, $SO_2R^3$ and $PO.(OR^3)_2$, wherein $R^3$ is alkyl or cycloalkyl, and $R^2$ is selected from the group consisting of H, F, Cl, $NO_2$, CN, alkyl, oxyalkyl, cycloalkyl, oxycycloalkyl, aryl and oxyaryl;

or wherein R and $R^1$ are joined together to form a cycloalkyl structure, or $R^1$ and $R^2$ are joined together to form a cycloalkyl or aryl structure, or R and $R^1$ as well as $R^1$ and $R^2$ are so joined, the two ring structures being fused, any of the aforesaid alkyl, cycloalkyl and aryl moieties optionally being substituted.

More preferably, the fluorination reaction is the fluorination of compounds having the general formula (B): RCO.CHR'CO.R" into compounds having the general formula RCO.CFR'CO.R". In these formulae, the group R may be alkyl, substituted alkyl, cycloalkyl, aryl, or substituted aryl, R' may be hydrogen, chlorine, nitro, cyano, alkyl, substituted alkyl, cycloalkyl, aryl, or substituted aryl, and R" may be alkyl, substituted alkyl, cycloalkyl, aryl, substituted aryl, OR, $NR_2$. Further, the groups R and R' may be joined together to form a cyclic structure. Where in the starting material for the fluorination reaction R' is H, the product of the reaction may have the formula $RCO.CF_2CO.R"$.

For the compounds of formulae A and B suitable substituents include R and $R^2$ groups or, as the case may be, R and R' groups; for example, alkyl may be substituted chlorine or fluorine), alkoxy and aryloxy, as well as other groups which are relatively inert to fluorine. Any of the aforegoing substituents may be substituted in turn by one or more other suitable substituents, to form groups such as, for example, haloalkoxy or alkoxyaryl.

The number of atoms in any of the groups R, $R^1$ and $R^2$ of formula (A), R, R' and R" of formula (B) and $R^1$ is not critical. since they play no part in the reaction. By way of example. however, the organic moieties may contain up to 10 carbon atoms, e.g. 1 to 4 carbon atoms. Cyclohexyl and cyclopentyl may be mentioned as a suitable cycloalkyl groups, and phenyl and naphthyl as suitable aryl groups, amongst others.

Methods Catalysed by Elemental Metal

In methods of this class. the catalyst is in the form of an elemental metal. A particular example of such a catalyst is metallic copper which may be used in the form of, for instance, a powder.

The carbonyl compound has an activating group in the β-position to the carbonyl group, like the preferred carbonyl reactants used with the transition metal compound catalysts. Indeed the preferred compounds described with reference to the transition metal compounds are preferred also for the metal catalysts. Most preferably, the compound is a β-dicarbonyl compound. Preferably, the β-dicarbonyl compound is a haloacetoacetate more preferably a chloroacetoacetate.

Preferably, the catalyst is used in a small amount. Particularly in the case of metallic copper, a preferred amount is up to 50 mg ($8 \times 10^{31\ 4}$ grams atom) per 100 ml of reactant solution, more preferably 10 to 30 mg ($1.6 \times 10^{-4}$ to $4.7 \times 10^{-4}$ grams atom) 100 ml solution and most preferably about 20 mg (3.15 grams atom) per 100 ml. Typically, the metal is used in an amount of up to 0.04 gram atoms and desirably up to 0.02 gram atoms, per mole of β-dicarbonyl compound, more preferably 0.004 to 0.012, especially about 0.008 gram atoms per mole of compound.

It is possible that the catalyst operates to speed up the enolisation of the compound carbonyl.

Reaction Conditions

Preferably, the reactions of the invention are conducted in the presence of a solvent. Preferred solvents include formic acid, acetic acid and acetonitrile, the latter being preferably used with a little water to give solubility to the salts.

Where fluorine is used as the fluorinating agent, it is preferably diluted with an inert gas such as nitrogen. Preferably, the fluorine is diluted to 1–50% v/v and, preferably in the range 5–20% v/v.

The temperature of the reaction is preferably 0–10° C.

The substrate may be used in a wide concentration range, preferably up to 400 grams/litre of solvent Examples of the present invention will now be described, by way of illustration only.

EXAMPLES

Example 1

By way of a control example, a reaction without any added salts was carried out. Thus, a glass reaction vessel fitted with a PTFE coated mechanical stirrer, a FEP (fluorinated ethylene-propylene) thermocouple well and FEP gas delivery tube was charged with ethyl-2-chloroacetoacetate (3.29 gm, 20 mmol.) and formic acid (50 ml) before being cooled to 5–8° C. The vessel was purged with nitrogen and then fluorine (32 mmol) diluted to 10% v/v with nitrogen was passed through the stirred solution over a period of two hours. At the end of this treatment, the fluorine supply was turned off and the reaction vessel. was purged with nitrogen. The reaction mixture was then poured into water and extracted with dichloromthane. The extracts were dried, evaporated and the colourless residue was analysed by glc which showed that 16% of the ethyl chloroacetoacetate had been converted into ethyl-2-chloro-2-fluoroacetoacetate.

A series of experiments was carried out to illustrate the effect of adding certain salts, in varying amounts, to the a reaction carried out as described above. The results of these experiments are shown in the following Table.

| Experiment No. | Salt added | Amt Salt added. mmol | g atom cation x 100 g mol substrate | Conversion, % |
|---|---|---|---|---|
| Control | — | — | — | 16 |
| Ex. 1 | Fe(NO$_3$)$_3$9H$_2$O | 0.4 | 2 | 54 |
| Ex. 2 | Fe(NO$_3$)$_3$9H$_2$O | 4.0 | 20 | 75 |
| Ex. 3 | Co(NO$_3$)$_2$6H$_2$O | 0.4 | 2 | 85 |
| Ex. 4 | NiSO$_4$6H$_2$O | 0.4 | 2 | 50 |
| Ex. 5 | Cu(NO$_3$)$_2$3H$_2$O | 0.4 | 2 | 90 |
| Ex 6 | Cu(OAc)$_2$H$_2$O | 0.4 | 2 | 84 |
| Ex 7 | Ni(NO$_3$)$_2$6H$_2$O | 4.0 | 20 | 53 |
| Ex 8 | Zn(NO$_3$)$_2$6H$_2$O | 0.4 | 2 | 62 |
| Ex 9 | Mn(NO$_3$)$_2$6H$_2$O | 0.4 | 2 | 60 |

Example 2

A glass reaction vessel fitted with a PTFE coated mechanical stirrer, an FEP thermocouple well and FEP gas delivery tube was charged with diethyl malonate (3.2 gm., 20 mmol.), cupric nitrate 3H$_2$O (0.48 gm., 2.0 mmol.) and acetonitrile (50 ml.) before being cooled to 5–8° C. The vessel was purged with nitrogen and then fluorine diluted to 10% v/v with nitrogen was passed through the stirred solution at a rate of 16 mmol/hour for 4 hours. At the end of the treatment, the fluorine supply was turned off and the reaction vessel was purged with nitrogen. The reaction mixture was then poured into water and extracted-with dichloromethane. A weighed amount of trifluoromethylbenzene was added to the extracts whose $^{19}$F nmr spectrum was then measured. The dried extracts were evaporated and the residue was analysed by glc and or $^1$H nmr. From this information, the amount of substrate converted (conversion) and yield of product, based on the amount of substrate converted were calculated. A sample of pure product was obtained by prepaurative scale gc and its identity was confirmed as diethyl-2-fluoromalonate {$\delta_H$ 1.41 (6H, t, J$_{HH}$ 7.13, CH$_3$), 4.42 (4H, q, J$_{HH}$ 7.2, CH$_2$), 5.36 (1H, d, J$_{HF}$ 48.3, CHF); $\delta_F$ 196.5 (d, J$_{HF}$ 48.2); $\delta_C$ 13.9 (s, CH$_3$), 62.7 (s, CH$_2$), 85.3 (d, $^1$J$_{CF}$ 196.6, CHF), 163.9 (d. $^2$J$_{CF}$ 24.1, CO); m/z (CI$^+$, NH$_3$) 196 ((M+NH$_4$)$^+$, 100%)}; Conversion 100%, Yield 78%.

Example 3

In an experiment carried out as described in Example 2 but in the absence of any transition metal compound, the conversion was less than 5%.

Example 4

An experiment was carried out as described in Example 2 using diethyl nitromalonate instead of diethyl malonate. Thus, 4.1 gm. (20 mmol.) diethylnitromalonate was treated with fluorine to give diethylfluoronitromalonate {$\delta_H$ 1.40 (6H, t, J$_{HH}$ 7.11, CH$_3$), 4.47 (4H, q, J$_{HH}$ 7.12, CH$_2$); $\delta_F$ 127.3 $\delta_C$ 13.7 (s, CH3), 65.2 (s, CH$_2$), 106.3 (d, $^1$J$_{CF}$ 261.7, CF), 157.9 (d. $^2$J$_{CF}$ 25.2, CO).} in 76% yield. The conversion was 97%.

Example 5

When the experiment in Example 4 was repeated in the absence of cupric nitrate 3H$_2$O, the conversion was ca. 12%.

Example 6

Example 2 was repeated using less copper nitrate and a shorter exposure to fluorine. Thus, 3.2 gm. (20 mmol.) diethylmalonate and 0.096 gm. (0.4 mmol.) copper (II) nitrate 3$_{H}$O in 50 ml acetonitrile were treated with 32 mmol. fluorine, diluted to 10% v/v with nitrogen, over 2 hours to give diethylfluoromalonate in high yield. Conversion. 88%.

Example 7

Example 6 was repeated using 0.116 gm. (0.4 mmol.) nickel nitrate 6H$_2$O instead of copper nitrate. Conversion 70%.

Example 8

Example 6 was repeated using ethyl acetoacetate instead of diethyl malonate. 45% of the ethyl acetoacetate reacted to give ethyl-2-fluoroacetoacetate in high yield (80%).

Example 9

When Example 8 was repeated in the absence of a compound of a transition metal, the conversion was 23%.

Example 10

Example 6 was repeated using N,N-diethylamino acetoacetamide instead of diethyl malonate. After this treatment, 59% of the N,Ndiethylamino acetoacetamide reacted to give N,N-iethylamino-2-fluoroacetoacetamide {(Found: C, 54.3; H, 8.1; N, 7.8. $C_8H_{14}NO_2$ requires C, 54.8; H, 8.0; N, 8.0.); $\delta_H$ 5.3 (d, $J_{HF}$ 49.9, 1H, —CHF—), 3.26 (m, 4H, $NCH_2CH_3$), 2.18 (d, J=4.0,.3H, $CH_3COCHF$), 1.08 (t, J=7.2, 3H, —$CH_2CH_3$), 1.00 (t, J=7.0, 3H, —$CH_2CH_3$); $\delta_F$ –188.7 (dd, $F_{HF}$ 49.5, $J_{HH}$ 4.3); $\delta_C$ 201.7 (d, $^2J_{CF}$ 24.0, $CH_3COCHF$—), 162.8 (d, $^2J_{CF}$ 20.2, CO.N<), 91.25 (d, $^1J_{CF}$ 194.9, CHF), 41.47 (s, $CH_2CH_3$), 40.41 (s, $CH_2CH_3$), 25.73 (s, $CH_3CO$), 13.90 (s, $CH_2C_3$), 12.20 (s, $CH_2CH_3$); m/z, 175}.

Example 11

When Example 10 was repeated in the absence of a compound of a transition metal, the conversion was 46%.

Example 12

Example 2 was repeated using ethyl cyanoacetate instead of diethyl malonate. After this treatment, 46% of the starting material was converted and the yield of ethyl cyanofluoroacetate {(HRMS ($NH_3$/CI*), Found: 149.0730; $C_5H_{10}FN_2O_2$ $(M+NH_4)^+$ requires 149.0726); $\delta_H$ 1.39 (t, $J_{H,H}$ 7.14, $CH_3$), 4.42 (q, $J_{H,H}$ 7.14, $CH_2$), 5.50 (d, $J_{H,F}$ 46.3, CHF); $\delta_F$ –194.6 (d, $J_{H,F}$ 46.3); $\delta_C$ 13.89 (s, CH3), 64.31 (s, ($CH_2$), 74.28 (d, $^1J_{C,F}$ 196.8 CFH), 111.62 (d, $^2J_{C,F}$ 29.8, CN), 160.64 (d, $^2J_{C,F}$ 24.7, CO).} was 50% and the yield of the ethyl cyanodifluoroacetate was 8%.
*CI=Chemical Ionisation

Example 13

When Example 12 was repeated in the absence of a compound of a transition metal, the conversion was ca. 12%.

Example 14

Example 2 was repeated using ethyl nitroacetate instead of diethyl malonate. After this treatment, 54% of the staring material was converted and the yield of ethyl nitrofluoroacetate { (HRMS ($CH_4$/CI), Found: 152.0312; $C_4H_7FNO_4$ $(M+1)^+$ requires 152.0391); $\delta_H$ 1.38 (t, $J_{H,H}$ 7.1, $CH_3$), 4.42 (q, $J_{H,H}$ 7.1, $CH_2$), 6.06 (d, $J_{H,F}$ 46.4, CHF); $\delta_F$ –150.5 (d, $J_{H,F}$ 48.4); $\delta_C$ 13.75 (s, CH3), 64.58 (s, ($CH_2$), 102.72 (d, $^1J_{C,F}$ 248.9 CFH), 159.0 (d, $^2J_{C,F}$ 24.8, CO).} was 52% and the yield of ethyl difluonitroacetate {$\delta_F$ –92.8 (s); $\delta_H$ 1.41 (t, $J_{H,H}$ 7.1, $CH_3$),4.49 (q, $J_{H,H}$ 7.1, $CH_2$); $\delta_C$ 13.6 (s, $CH_3$), 65.8 (s, (CH2), 112.9 (t, $^{1J}_{C,F}$ 297.5 CF2), 155.9 (t, $^2J_{C,F}$ 31.3, CO).} was 21%.

Example 15

When Example 14 was repeated in the absence of a salt of a transition metal, the conversion was ca. 12%.

Example 16

Example 2 was repeated using 4,4-dimethyl-3-oxo-2-pentane nitrile instead of dietiyl malonate. After this treatment, 70% of the starting material had reacted and the yield of 4,4dimethyl-3-oxo-2-fluoropentane nitrile { (HRMS ($NH_3$/CI), Found: 161.1090; $C_7H_{14}FN_2O$ $(M+NH_4)^+$ requires 161.1090); $\delta_H$ 1.31 (9H, s), 5.69 (1H, d, $J_{H,F}$ 47.0); $\delta_F$ –192 (d, $J_{H,F}$ 47.0); $\delta_C$ 25.76 (d, $^4J_{C,F}$ 2.3, $CH_3$), 44.29 (d, $^3J_{C,F}$ 2.7, $(CH_3)_3C$), 79.08 (d, $^1J_{C,F}$ 199.2, CFH), 112.29 (d, $^2J_{C,F}$ 29.7, CN), 200.59 (d, $^2J_{C,F}$ 17.9, CO).} was 52%.

The yield of 4,4-dimethyl-3-oxo-2,2-difluoropentane nitrile {$\delta_F$ –94.2 (s); $\delta_H$ 1.34 (s); $\delta_C$ 30.02 (s, $CH_3$), 47.68 $(CH_3)_3C$)109.63 (t, $^1J_{C,F}$ 262.47 $CF_2$), 114.25 (t, $^2J_{C,F}$ 42.14, CN), 200.40 (t, $^2J_{C,F}$ 25.34, CO); m/z ($CI^+$, $CH_4$) 162 (M+1).} was 13%

Example 17

When Example 16 was repeated in the absence of a salt of a transition metal, the conversion was ca. 15%.

Example 18

Example 2 was repeated using dimethyl-2-oxypropyl phosphonate instead of diethyl malonate. After this treatment, 95% of the starting material was converted and the yield of dimcthyl-1-fluoro-2-oxypropyl phosphonate (purified by column chromatography; $SiO_2$/ethyl acetate){ (HRMS, Found: $(M+NH_4)^+$ 202.0644 $C_5H_{14}FNO_4P$ requires 202.06445); $\delta_H$ 2.39 (3H, d, $^4J_{H,F}$ 4.5, $CO.CH_3$), 3.9 (6H, d, d, $^2J_{H,P}$ 10.8, J 2.9, $CH_3OP$), 5.25 (1H, d,d, $^2J_{H,F}$ 47.7, $^2J_{H,P}$ 14.4, CHF); $\delta_F$ –208 (d,d,q, $^2J_{F,P}$ 71.3, $^2J_{H,F}$ 47.8, $^4J_{H,F}$ 4.5); $\delta_P$ 12.7 (d, $^2J_{F,P}$ 71.2); $\delta_C$ (50 MHz) 26.5 (s, $CH_3O.C$), 54.2 (d,d, $^2J_{C,P}$ 6.6, $^4J_{C,F}$ 2.0, $CH_3OP$), 91.0 (d,d, $^1J_{C,F}$ 196.5, $^1J_{C,P}$ 152.5 CHF), 200.5 (d, $^2J_{C,F}$ 20.2, CFHCO); m/z ($CI^+$, $NH_3$) 202 ($(M+NH_4)^+$, 10%), 128 (100).} was 20% and the yield of dimethyl-1,1-difluoro-2-oxypropyl phosphonate was ca.5%.

Example 19

When Example 18 was repeated in the absence of a salt of a transition metal, the conversion was ca. 5%.

Example 20

Example 2 was repeated using methanesulphonylpropan-2-one instead of diethyl malonate. After this treatment. 95% of the storing material was converted and the yield of 1-fluoro-1-methanesuphonylpropan-2-one purified by column chromatography; $SiO_2$/dichloromethane) {(Found: C, 31.0; H, 4.4. $C_4H_7FO_3S$ requires C, 31.2; H, 4.5%, HRMS, Found; $(M+NH_4)^+$ 172.0444 $C_4H_{11}FNO_3S$ requires 172.04437); $\delta_H$ 2.5 (3H, d, $^4J_{H,F}$ 3.6, $CO.CH_3$), 3.1 (3H, d, $^4J_{H,F}$ 2.2 $SO.CH_3$), 5.6 (1H, d, $^2J_{H,F}$ 48.0, CHF); $\delta_F$ –183.7 (dm, $^2J_{H,F}$ 4714.0); $\delta_C$ 27.8 (s, $CH_3S$), 38.1 (s, $CH_3C$), 100.4 (d, $^1J_{C,F}$ 231,CHF), 196.0 (d, $^2J_{C,F}$ 20.4, CO); m/z ($CI^+$, $NH_3$) 172 $((M+NH_4)^+$, 100%).} was 45% and the yield of 1,1-difluoro-1-methanesuphonylpropan-2-one { $\delta^F$ –113.3 (s); m/z ($CI^+NH_3$) 190 $((M+NH_4)^+$, 100%).} was ca. 5%.

Example 21

When Example 20 was repeated in the absence of a salt of a transition metal, the conversion was ca. 14%.

Example 22

To a solution of 5.0 g ethyl chloroacetoacetate in 100 ml formic acid was added 20 mg of copper powder. This was stirred at 3° C. while a gaseous mixture of nitrogen (60 ml/min) and fluorine (6.7 ml/min) was passed through for 6 hours. The reaction mixture was periodically analysed by GC by taking out an aliquot, drowning into water and extracting with dichioromethane. The results are shown in Table 1 and in FIG. 1 of the accompanying drawings.

TABLE 1

| Time in hours | GC results - integration % conversion |
| --- | --- |
| 1 | 20.0 |
| 1.5 | 25.7 |
| 2 | 35.7 |
| 2.5 | 42.9 |
| 3 | 55.6 |
| 3.5 | 60.4 |
| 5 | 78.8 |
| 6 | 87.3 |

Example 23

Figure 2:
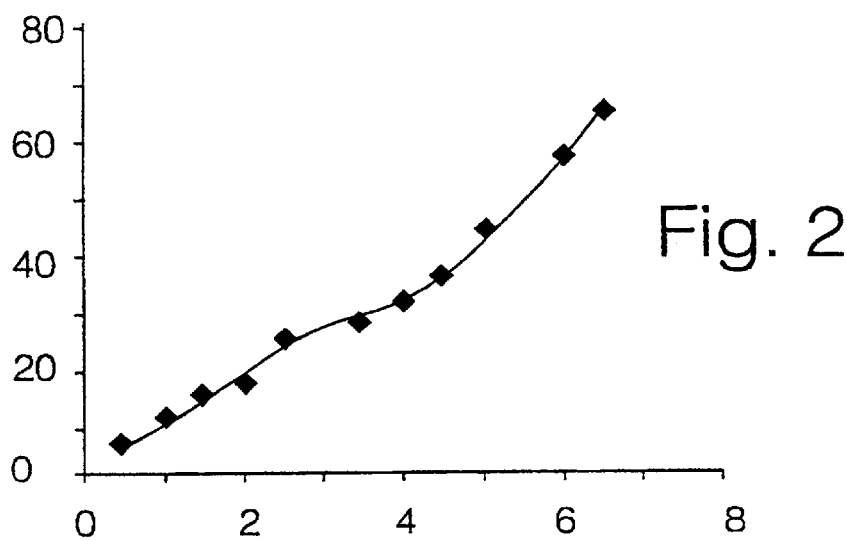

The same procedure was used as in Example 22, except that 20 mg of copper powder were added to the reaction solution after it had proceeded for 4.5 hours. The results in this case are given in Table 2 and in FIG. 2 of the accompanying drawings.

TABLE 2

| Time in hours | GC results - integration % conversion |
| --- | --- |
| 0.5 | 7.1 |
| 1 | 12.2 |
| 1.5 | 16.5 |
| 2 | 19.9 |
| 2.5 | 24.9 |
| 3.5 | 28.6 |
| 4 | 33.2 |
| 4.5 | 37.3 |
| 20 mg of copper powder added | |
| 5 | 44.0 |
| 6 | 58.2 |
| 6.4 | 65.7 |

Example 24

Figure 3:
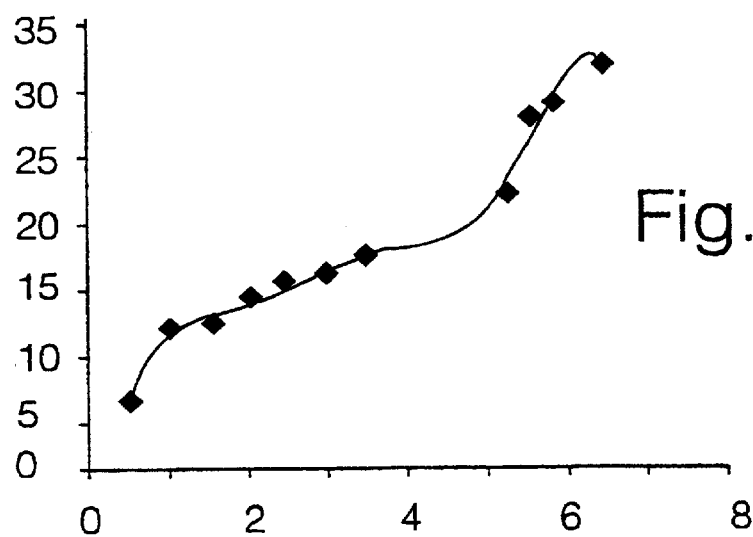

The same procedure was used as in Example 22, except that 1 g of copper powder was added at the beginning of the reaction and a further 1 g after 5.25 hours. The results are given in Table 3 and in FIG. 3 of the accompanying drawings.

TABLE 3

| Time in hours | GC results integration % conversion |
| --- | --- |
| copper added | |
| 0.5 | 6.2 |
| 1 | 12.0 |
| 1.5 | 12.5 |
| 2 | 14.4 |
| 2.5 | 15.3 |
| 3 | 15.8 |
| 3.5 | 16.7 |
| 5.25 | 22.3 |
| 1 g of copper powder added | |
| 5.5 | 27.5 |
| 5.6 | 28.4 |
| 6.5 | 32.6 |

Example 25

Figure 4:
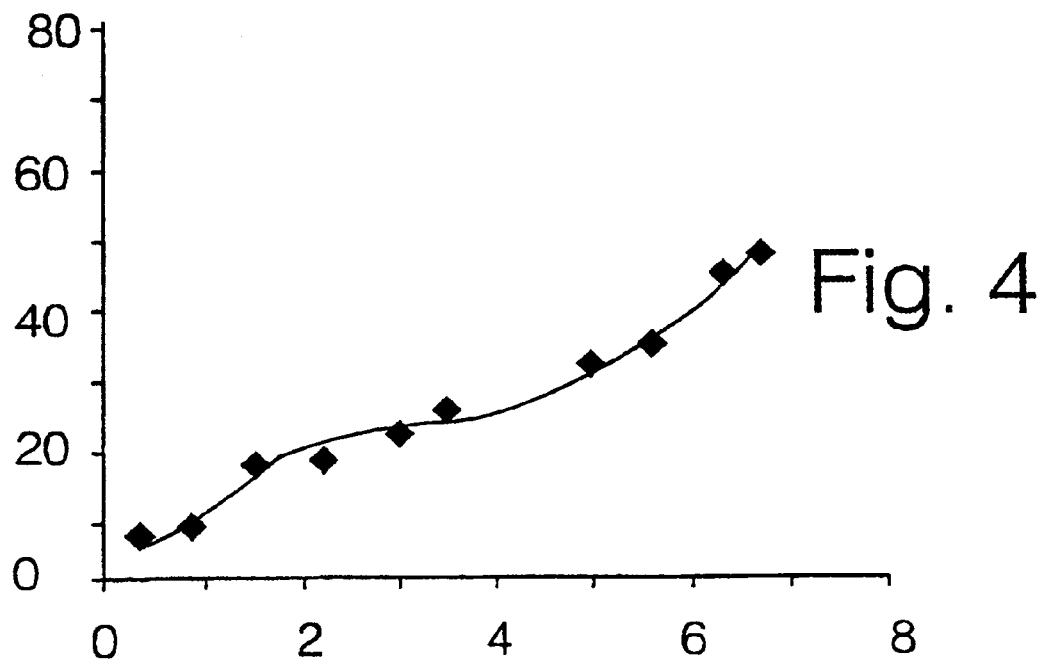

The same procedure was used as in Example 22, except that 1 g of copper powder was added to the reaction after 6 hours. The results are given in Table 4, and in FIG. 4 of the accompanying drawings.

TABLE 4

| Time in hours | GC results - integration % conversion |
| --- | --- |
| 0.3 | 6.6 |
| 0.8 | 8.9 |
| 1.5 | 18.0 |
| 2.2 | 18.4 |
| 3 | 21.1 |
| 3.5 | 24.5 |
| 5 | 31.7 |
| 5.7 | 34.2 |
| 1 g copper powder added | |
| 6.3 | 43.1 |
| 6.7 | 47.2 |

Example 26

Figure 5:
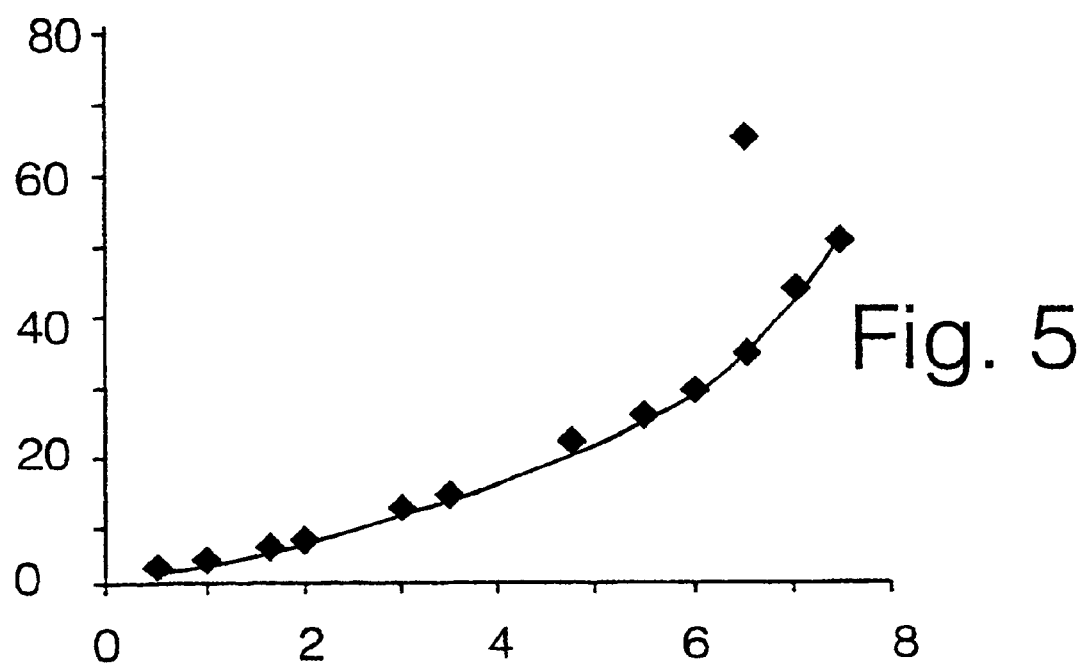

The same procedure was used as in Example 22, except that 30 mg of potassium fluoride were added at the beginning of the reaction and 20 mg of copper powder were added after 5.5 hours. The results are given in Table 5 and in FIG. 5 of the accompanying drawings.

TABLE 5

| Time in hours | GC results - integration % conversion |
| --- | --- |
| 0.5 | 2.7 |
| 1 | 4.4 |
| 1.77 | 7.7 |
| 2 | 8.9 |
| 3 | 12.0 |
| 3.5 | 13.9 |
| 4.8 | 21.6 |
| 5.5 | 26.4 |
| 20 mg of copper powder added | |
| 6 | 29.1 |
| 6.5 | 35.0 |
| 7 | 43.9 |
| 7.4 | 50.2 |

The above examples 22–26 show that when very small amounts of metallic copper are added, the reaction is speeded up. This occurs both when the copper is added from the start (Example 22) and when the copper is added part-way through the reaction (Example 23). If, however, a larger quantity (about 1 g per 100 ml) is added during the reaction (Examples 24 and 25), there is an initial increase in rate, following which the reaction slows down again. If a larger quantity of copper is added at the start there is no catalyst at all (Example 24).

Example 26 investigates the possibility that the reaction is being catalysed by base, for instance fluoride ion from copper fluoride. Traces (30 mg) of potassium fluoride were added at the beginning of the reaction. There was no reaction rate increase but rather a slowing down. Addition of 20 mg of copper powder after 5.5 hours resulted in an increase in the reaction rate.

What is claimed is:

1. A method of fluorinating a carbonyl compound by replacement of a hydrogen atom at the α-position with fluorine comprising reacting the carbonyl compound with a fluorinating agent in the presence of a catalytically effective amount of a transition metal-containing catalyst, the carbon atom which is substituted by fluorine being attached to an activating group additional to said carbonyl group when the transition metal-containing catalyst is an elemental transition metal.

2. A method according to claim 1 wherein the compound is a salt of copper, iron, cobalt, nickel, manganese, or zinc.

3. A method according to claim 1, wherein the transition metal compound is present in the range of from 0.2 to 25 gram atoms of transition metal ion to 100 moles of carbonyl compound.

4. A method according to claim 1, wherein the transition metal compound is ferric nitrate, cobalt nitrate, nickel sulphate or copper nitrate.

5. A method according to claim 2, wherein the carbon atom which is substituted by fluorine is also attached to an activating group selected from the group consisting of a CO group, $(R^1O)_2PO, SO_2$, and CN, wherein $R^1$ is selected from the group consisting of $COR^3$, $COOR^3$, $NO_2$, CN, $CONR^3_2$, $SO_2R^3$, and $PO(OR^3)_2$, wherein $R^3$ is alkyl or cycloalkyl.

6. A method according to claim 5 wherein the carbonyl compound is an α-substituted carbonyl compound having the general formula $RCO.CHR^1.R^2$, where:

R is selected from the group consisting of alkyl, oxyalkyl (—O—alkyl), cycloalkyl, oxycycloalkyl, aryl and oxyaryl;

$R^1$ is selected from the group consisting of $CO.R^3$, $CO.OR^3$, $NO_2$, CN, $CO.NR^3_2$, $SO_2R^3$ and $PO.(OR^3)_2$, wherein $R^3$ is alkyl or cycloalkyl, and $R^2$ is selected from the group consisting of H, F, C, $NO_2$, CN, alkyl, oxyalkyl, cycloalkyl, oxycycloalkyl, aryl and oxyaryl;

or wherein R and $R^1$ are joined together to form a cycloalkyl structure, or $R^1$ and $R^2$ are joined together to form a cycloalkyl or aryl structure, or R and $R^1$ as well as $R^1$ and $R^2$ are so joined, the two ring structures being fused, any of the aforesaid alkyl, cycloalkyl and aryl moieties optionally being substituted.

7. A method according to claim 6 wherein the carbonyl compound is of the formula RCO.CHR'COR" where R is selected from the group consisting of alkyl, substituted alkyl, cycloalkyl, aryl and substituted aryl, R' is selected from the group consisting of hydrogen, chlorine, nitro, cyano, alkyl, substituted alkyl, cyclo alkyl, aryl and substituted aryl, and R" is selected from the group consisting of alkyl, substituted alkyl, cyclo alkyl, aryl, substituted aryl, OR and $NR_2$ or wherein the groups R and R' are joined together to form a cyclic structure.

8. A method according to claim 6 wherein R is selected from the group consisting of alkyl, oxyalkyl, cycloalkyl and oxycycloalkyl, any of the aforesaid moieties optionally being substituted.

9. A method according to claim 6, wherein $R^2$ is selected from the group consisting of H, alkyl, oxyalkyl, cycloalkyl and oxycycloalkyl, aryl and oxyaryl, any of the aforesaid moieties optionally being substituted.

10. A method according to claim 6, wherein $R^1$ is selected from the group consisting of $COR^3$ and $CooR^3$.

11. A method according to claim 6, wherein any one or more of R, $R^1$, $R^2$, $R^3$, R' and R" contains up to 10 carbon atoms.

12. A method according to claim 1 wherein the carbonyl compound is a β-dicarbonyl compound.

13. A method according to claim 12 wherein the catalyst is in the form of elemental metal.

14. A method according to claim 13 wherein the catalyst is metallic copper in powder or another form.

15. A method according to claim 13, wherein the elemental metal is used in an amount of no more than 0.04 gram atoms per mole of β-dicarbonyl compound.

16. A method according to claim 12 wherein the β-dicarbonyl compound contains a carbon atom which is substituted by fluorine which is also attached to an activating group selected from the group consisting of a CO group, $(R^1O)_2PO, SO_2$, and CN, wherein $R^1$ is selected from the group consisting of $COR^3$, $COOR^3$, $NO_2$, CN, $CONR^3_2$, $SO_2R^3$, and $PO(OR^3)_2$, wherein $R^3$ is alkyl or cycloalkyl and optionally is a haloacetoacetate.

17. A method according to claim 16 wherein the haloacetate is a chloroacetoacetate.

18. A method according to claim 1 wherein the fluorinating agent is elemental fluorine.

19. A method according to claim 18 wherein the fluorinating agent is fluorine gas diluted with an inert gas.

20. The method according to claim 19 wherein the fluorine gas is diluted to 1–50 v/v.

21. A method according to claim 1 wherein the reaction temperature is 0–10° C.

22. A method according to claim 1 wherein the carbonyl compound is initially present in an amount up to 400 grams/litre of solvent.

23. A method of fluorinating a 1,3-dicarbonyl compound comprising reacting the 1,3-dicarbonyl compound with a fluorinating agent in the presence of a salt of a transition metal.

24. A method according to claim 23 wherein the transition metal compound is a salt of copper, iron, cobalt, manganese or zinc.

25. A process for the fluorination of a β-dicarbonyl compound by means of a fluorinating agent, the process being carried out in the presence of a transition metal-containing catalyst.

26. A process according to claim 25 wherein the transition metal catalyst is an elemental metal.

27. A process according to claim 1, further comprising the step of subjecting the fluorine-substituted compound to a process to make a subsequent end product therefrom.

* * * * *

UNITED STATES PATENT AND TRADEMARK OFFICE
CERTIFICATE OF CORRECTION

PATENT NO. : 6,300,511 B1  
DATED : October 9, 2001  
INVENTOR(S) : Richard Dickinson Chambers; John Hutchinson; John Stewart Moilliet It is certified that error appears in the above-identified patent and that said Letters Patent is hereby corrected as shown below:

Column 9,  
Line 28, after "F," delete "C" and replace with -- Cl --

Column 10,  
Line 4, after "COR$^3$ and" delete "CooR$^3$" and replace with -- CO.OR$^3$ --

Signed and Sealed this

Twelfth Day of March, 2002

*Attest:*

JAMES E. ROGAN  
*Attesting Officer*     *Director of the United States Patent and Trademark Office*